United States Patent [19]
Koblanski

[11] Patent Number: 5,335,661
[45] Date of Patent: Aug. 9, 1994

[54] ULTRASONIC SCANNING APPARATUS

[76] Inventor: John N. Koblanski, 1205 - 4160 Sardis St., Burnaby, British Columbia, Canada, V5H 1K2

[21] Appl. No.: 18,709

[22] Filed: Feb. 17, 1993

[51] Int. Cl.⁵ .............................. A61B 8/00
[52] U.S. Cl. .............................. 128/661.03
[58] Field of Search ........... 128/660.01, 660.02, 128/661.03, 915; 73/599, 602

[56] References Cited

U.S. PATENT DOCUMENTS

| | | | |
|---|---|---|---|
| 3,480,002 | 11/1969 | Flaherty et al. | 128/915 X |
| 4,167,180 | 9/1979 | Kossoff | 128/915 X |
| 4,222,274 | 9/1980 | Johnson | 128/915 X |
| 4,282,880 | 8/1981 | Gardineer et al. | 128/915 X |
| 4,433,690 | 2/1984 | Green et al. | 128/915 X |
| 4,455,872 | 6/1984 | Kossoff et al. | 128/915 X |
| 4,509,368 | 4/1985 | Whiting et al. | 128/915 X |
| 5,197,475 | 3/1993 | Antich et al. | 128/660.01 |

*Primary Examiner*—Francis Jaworski
*Attorney, Agent, or Firm*—Daniel L. Dawes

[57] ABSTRACT

Apparatus to measure the physical characteristics of an object. The apparatus has a bath to receive the object. The object can be stabilized and control in its position in the bath. Liquid is supplied to and from the bath. The temperature of that liquid can be controlled so that is above the temperature of the object. There is an ultrasonic transmitter to send a signal through the object and an ultrasonic receiver to receive the signal. The velocity of the signal through the object can be calculated. In a preferred embodiment, the object is a foot and the apparatus is useful in diagnosing osteoporosis.

16 Claims, 5 Drawing Sheets

ULTRASONIC SCANNING APPARATUS

FIELD OF THE INVENTION

This invention relates to an apparatus to measure the physical characteristics of an object. It finds particular application in measuring the physical characteristics of bone and is thus of value in diagnosing osteoporosis.

The present apparatus finds application in measuring the density and elasticity of a material. The apparatus also finds application in measuring material homogeneity, rate of settling of a suspension and the degree of gaseous saturation. However, and as indicated, it finds particular application in the diagnosis of osteoporosis.

DESCRIPTION OF THE PRIOR ART

Osteoporosis is a common disease. It is characterized by deterioration of the bone. The bones become porous and brittle. Osteoporosis is diagnosed by measuring the density and elasticity of the bone. High density alone does not determine the bone's resistance to fracture. The bone can possess quite high density but still be brittle and therefore susceptible to breakage.

To determine the degree of elasticity a measurement of sound velocity in the bone can be carried out. The following relationship applies:

$$E = \sqrt{\frac{V^2}{D}}$$

where E is the elasticity, V the velocity of sound and D is the density.

The density of bone can be measured from the attenuation of sound within it.

Ultrasound has been used to diagnose osteoporosis but its use has been unreliable, difficult and time consuming. The measurement of density and elasticity of human bone in vivo, has lacked the necessary degree of accuracy to diagnose osteoporosis definitively. Quite high accuracy is needed to measure the small change in density and velocity to make a correct diagnosis. In the main the problems of reliability stem from the unpredictable transfer of ultrasound energy to the bone. The transducers used are not perfectly flat and the surface of the test object, human skin, also has an irregular surface. As a result air is trapped between the transducer face and the skin. This air gap presents a high impedance, resulting in the partial or complete reflection of the sound back into the transducer. To avoid this problem liquids have been used to displace the air. Water has been found to be the most practicable. However, the methods of using the liquids have been such that air bubble formation commonly occurs, yielding inaccurate measurement both for sound velocity and attenuation.

The prior art methods use a transducer to both send and receive. Both the transmitter and the receiver are of the same size but the area for receiving the sound energy is the entire face. The efficiency of the transducer varies across its face thus a relatively high proportion of the received energy could arrive at an area of the transducers having a low sensitivity, producing inaccurate results.

Furthermore prior methods used for centering the heel relative to the transmitter and the receiver are poor. A typical prior art method uses X-rays which is considered hazardous and expensive. Methods of measuring the heel bone are largely ignored, resulting in the ultrasound being refracted around the bone to yield a false, low value of bone density.

Other methods involve external calipers to measure the bone thickness. However the pressure of the calipers varies, giving false thickness and therefore poor velocity measurements.

It has also been assumed that the velocity of sound in a particular liquid was constant whereas the velocity varies with the amount of trapped gases within the medium. The erroneous assumption led to instruments being built having a fixed distance between the transmitter and receiving device and no contact with the test object. Although this would seem to avoid the problems concerning uneven surfaces, it took no account of gases contained within the liquid.

Prior art methods required a frequency analyzer when more than one frequency was used to measure attenuation. Such a procedure substantially increases costs.

SUMMARY OF THE INVENTION

The present invention seeks to address the above problems and provide an apparatus able to give accurate information concerning bone.

Accordingly, and in a first aspect, the invention is an apparatus to measure the physical characteristics of an object, the apparatus comprising a bath to receive the object; means to stabilize and control the position of the object in the bath; means to supply liquid to and from the bath; means to control the temperature so that the liquid temperature is above the temperature of the object; an ultrasonic transmitter to send a signal through the object; an ultrasonic receiver to receive the signal; and means to determine the velocity of the signal through the object.

DESCRIPTION OF THE PREFERRED EMBODIMENTS

The drawing show an apparatus to measure the physical characteristics of an object. The apparatus has a main body 10 having a recess that defines a bath 12 to receive the object. The illustrated embodiment is designed to hold a foot, that is to say the object is a foot, and as such the illustrated apparatus is of particular application in the diagnosis of osteoporosis.

Figure 2:
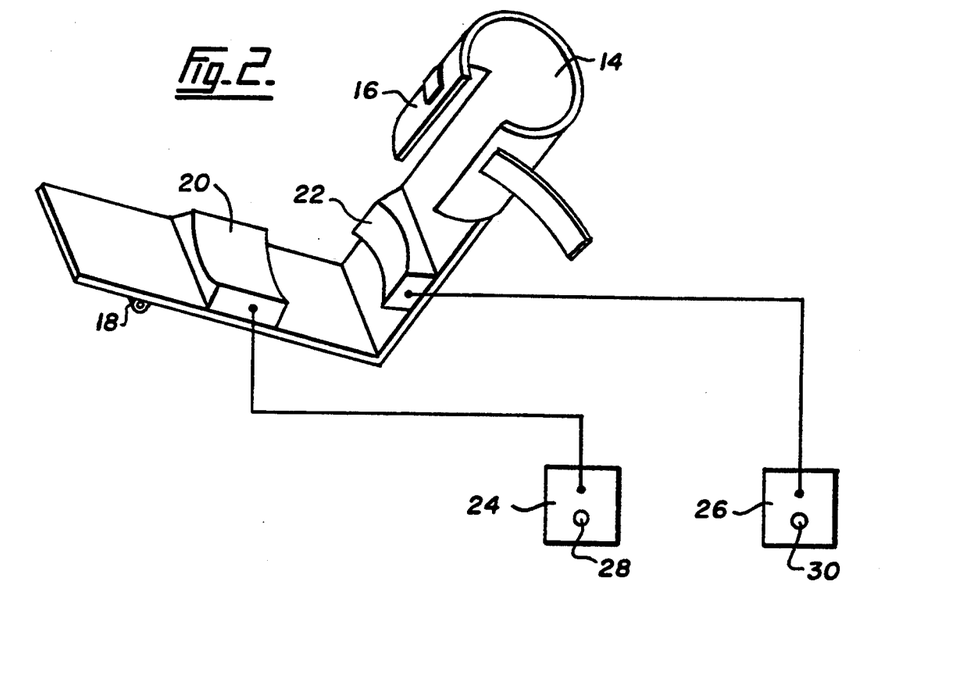
FIG. 2 is a detail of FIG. 1.

The bath 12 includes means to stabilize and control the position of the foot. There is a brace 14 which is a simple right-angled body with a strap 16 to go around the leg to hold the foot in the brace 14. The brace 14 is pivotally mounted in the bath by a simple housing 18 to receive a pin (not shown). The foot is located in the brace 14 by a first bladder 20 to contact the sole of the foot and a second bladder 22 to contact the ankle of the foot. As shown particularly in FIG. 2 there is a fluid supply to the bladders 20 and 22. The fluid supply comprises reservoirs 24 and 26, located in the body 10 with pumps (not shown), to pump fluid, usually water, to inflate and deflate the bladders 20 and 22 to control the position of the foot. Push buttons 28 and 30 are used to apply power to the pumps 24 and 26.

Figure 3:
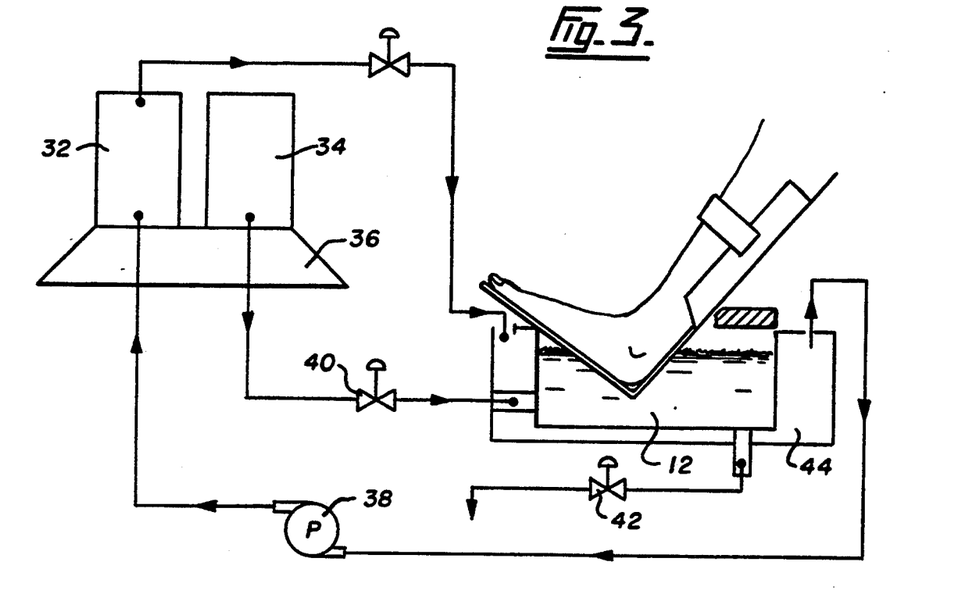
FIG. 3 is a further detail of FIG. 1.

The bath 12 holds a liquid, usually water. As shown in FIG. 3 the liquid is contained in reservoirs 32 and 34 shown positioned on a stand 36 received in the body 10. There is a pump 38 to pump water to and from the reservoirs 32 and 34 and motorized control valves 40 to direct the flow of the liquid. There is a further motorized valve 42 through which the bath 12 can be drained. There is a heated jacket or heat exchanger 44 surrounding the bath 12 so that the liquid in the bath can be kept at a controlled, constant temperature.

That controlled, constant temperature is above the temperature of the heel and at such a level that dissolved gases are not driven from the liquid at the heel surface.

Figure 1:
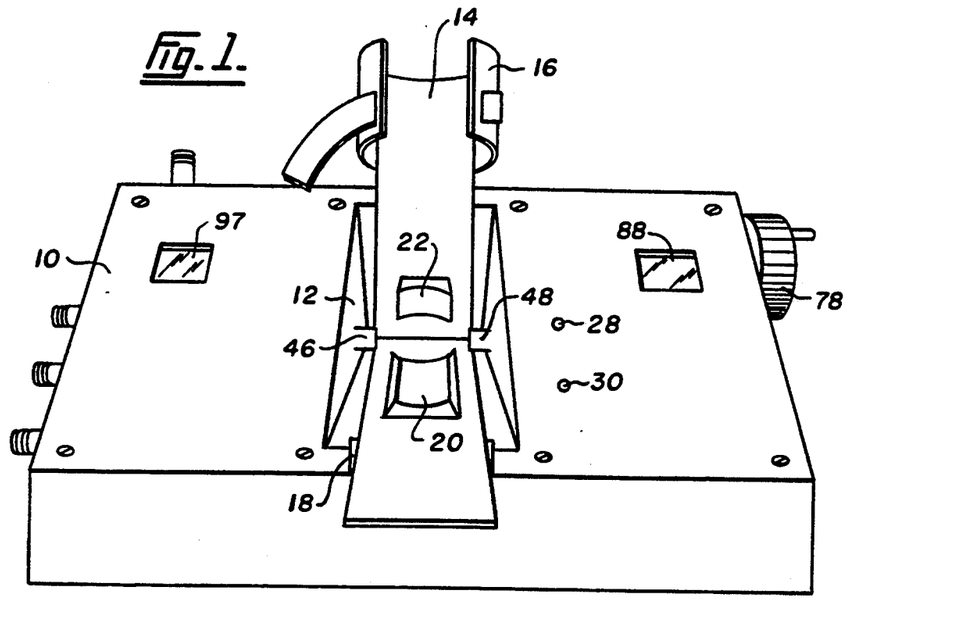
FIG. 1 is a general view of the apparatus according to the present invention.

FIG. 1 shows an ultrasonic transmitter 46 in the bath 12 to send a signal through the foot. On the opposite side of the bath 12 there is an ultrasonic receiver 48. The transmitter and the receiver will, typically, be piezoelectric ceramic transducers.

Figure 4:
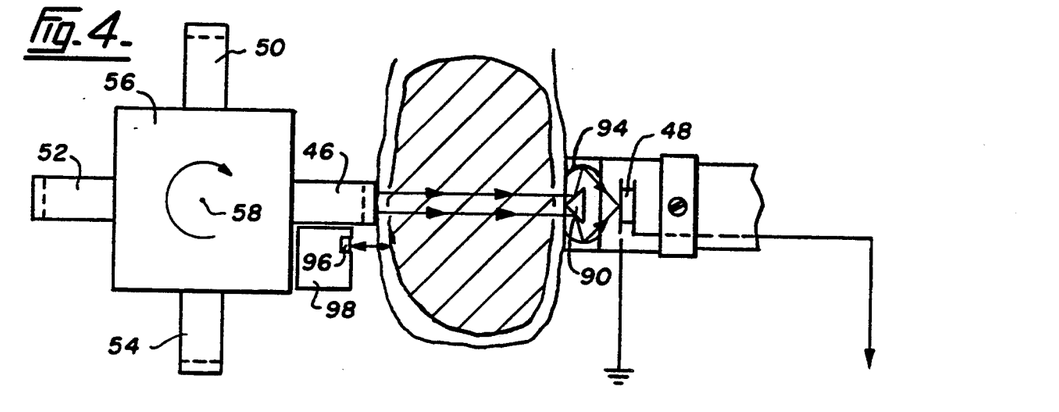
FIG. 4 illustrates use of the apparatus of the present invention.
Figure 5:
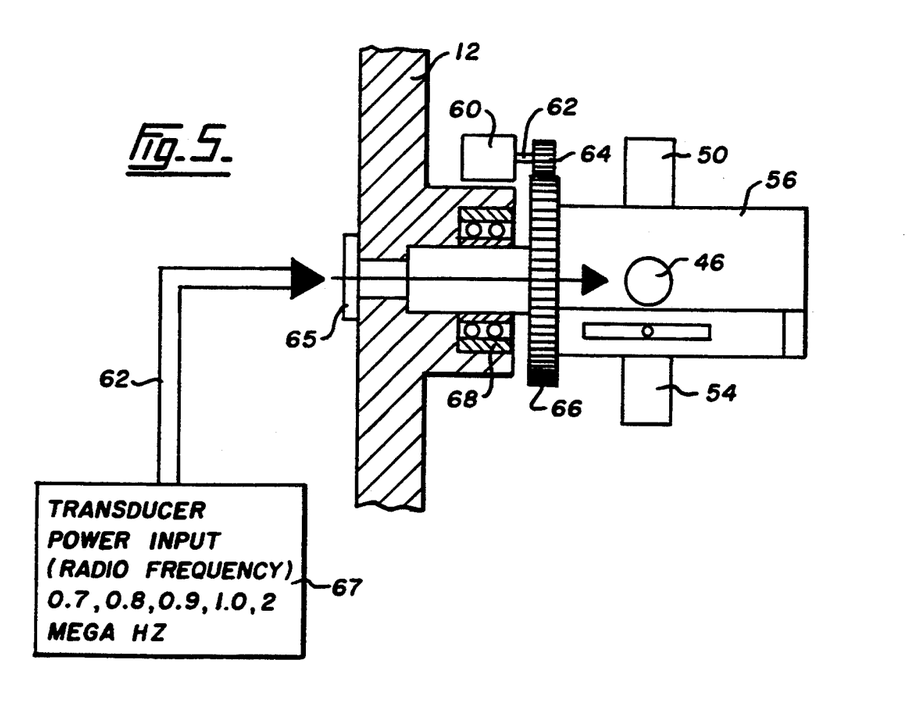
FIG. 5 shows a means of varying the transmitter.

As shown particularly in FIGS. 4 and 5 there are a plurality of transmitters 46, 50, 52, 54 mounted on a housing 56. Each transmitter is able to transmit a signal of different frequency. For example the transmitter 46 may be able to transmit a signal with a frequency of 1 megahertz, transmitter 50 transmits a signal with a frequency of 0.9 megahertz, transmitter 52 transmits a signal of 0.8 megahertz and transmitter 54 transmits a signal with a frequency of 0.7 megahertz. Which transmitter is effective is determined by making the housing 56 rotatable about its axis 58, as shown by the arrow in FIG. 4.

To achieve the necessary rotation of the housing 56 a step motor 60 is mounted in the housing 12. Motor 60 has an output shaft 62 with a gear wheel 64 on that shaft. Gear wheel 64 engages a second, much larger, gear wheel 66 mounted on the housing 56. That is the two gear wheels 64 and 66 constitute a transmission whereby the rotation of the step motor 60, on receipt of electric current, can be used to rotate the housing 56 through the transmission.

Power for the transmitter is applied through the linkage 62, passing through a rotating support 65 from a power unit 66.

Support 65 rotates in bearing 68. There is also means to reciprocate the receiver 48 towards and away from the transmitter 46. As shown particularly in FIG. 6 the receiver 48 is mounted on a shaft 68 having a thread 70 received in a threaded housing 72. There is a first gear wheel 74 mounted on the shaft 68 and a drive shaft 76 to be turned by hand by hand wheel 78. There is a second gear wheel 80 on the drive shaft 76 to engage the first gear wheel 74. Thus rotation of the drive shaft 76 by hand rotates the shaft 68 to reciprocate the shaft 68, and thus the receiver 48, relative to the transmitter 46. Bearing 82 supports shafts 68 and 76.

Figures 4A, 6:
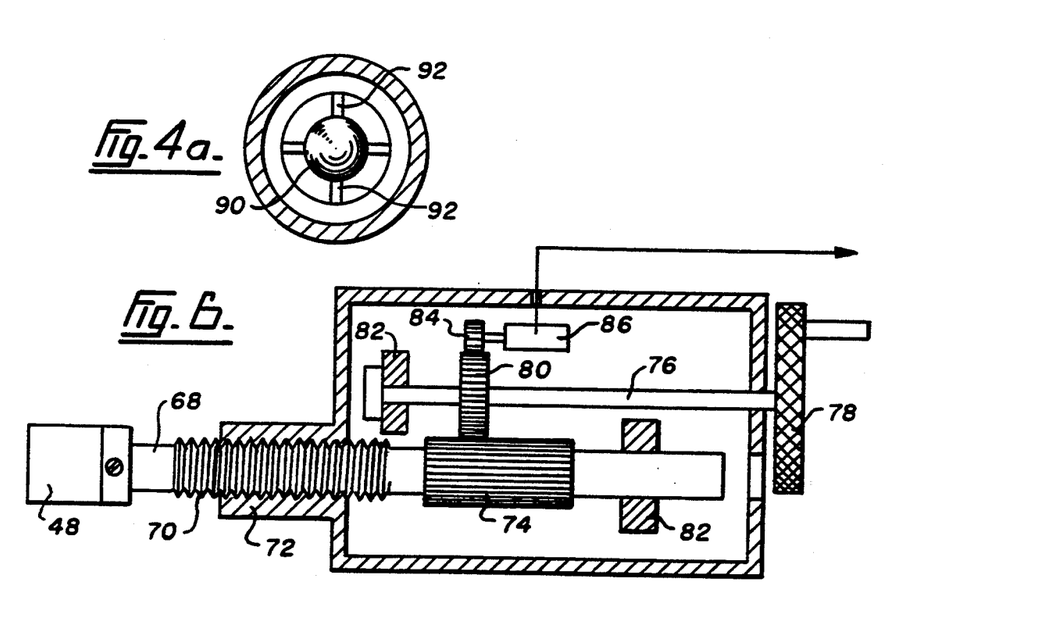
FIG. 4a illustrates a detail of FIG. 4.
FIG. 6 illustrates variation of the position of the receiver.

The distance moved by the receiver 48 is recorded by the use of a gear wheel 84 in contact with the gear wheel 80 and driving revolution counter 86. Output from the revolution counter 86 is displayed at a window 88 in the main body.

The apparatus includes means to focus the sound on to the receiver 48. As shown particularly in FIGS. 4 and 4a that means comprises a conical deflector 90 upstream of the receiver 48 and carried by supports 92. There is parabolic reflector 94 adjacent the conical deflector 90 to direct the sound to the receiver 48.

The focusing function is not simply to intensify the sound energy at the receiver but to limit the area of the receiver to a central point. Thus all the energy falls on the most sensitive area as well as the area furthest away from the periphery at which the mounting occurs. This peripheral area is most sensitive to changes in the mounting apparatus due to temperature and the like.

There is a transmitter/receiver unit 96 able to transmit a signal towards the foot and to receive the reflected signal. That signal, which typically has a frequency of 2 megahertz, is such that it can penetrate soft tissue, for example flesh and skin of the ankle but not bone. It is reflected by the bone. The result is shown in readout 97 of body 10

Figure 7:
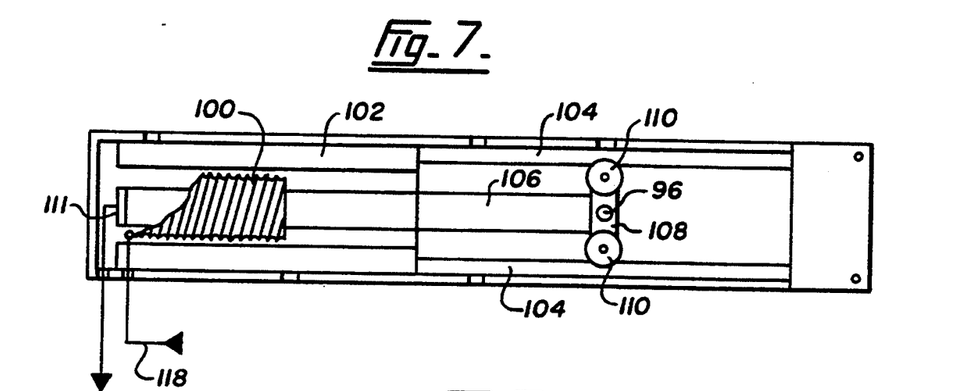
FIG. 7 and FIG. 7a show the use of an additional transmitter receiver unit.
Figure 7A:
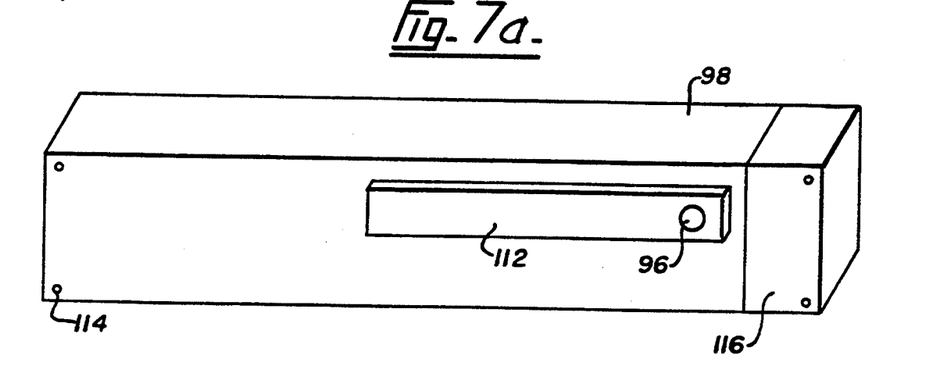

Apparatus associated with the transmitter/receiver 96 is shown in FIGS. 7 and 7a. It comprises a housing 98 that includes a motor 100. There is a permanent magnet 102 at the internal periphery of the housing 98 and a rail guide 104 for the magnet 102. An actuator arm 106 extends from the motor 100 to a bracket support 108 for the transducer 96. There are wheels 110 mounted on the bracket support 108. There is a position sensor 111. that produces output. There is a transparent window 112, for example of methacrylate, to allow passage of the ultrasonic signal but to seal the interior of the housing 98. The housing 98 is attached to the housing 56, (FIG. 4) by screws 114. There is a temperature controlled electronic cooling device 116 and a power supply for the motor 100 enters through line 118. Device 116 uses a semi-conductor controlled by a current flow, an application of the Peltier effect in which heat is absorbed by passage of a current through a junction of two metals. Passage one way absorbs heat, passage in the other direction generates heat.

Figure 8:
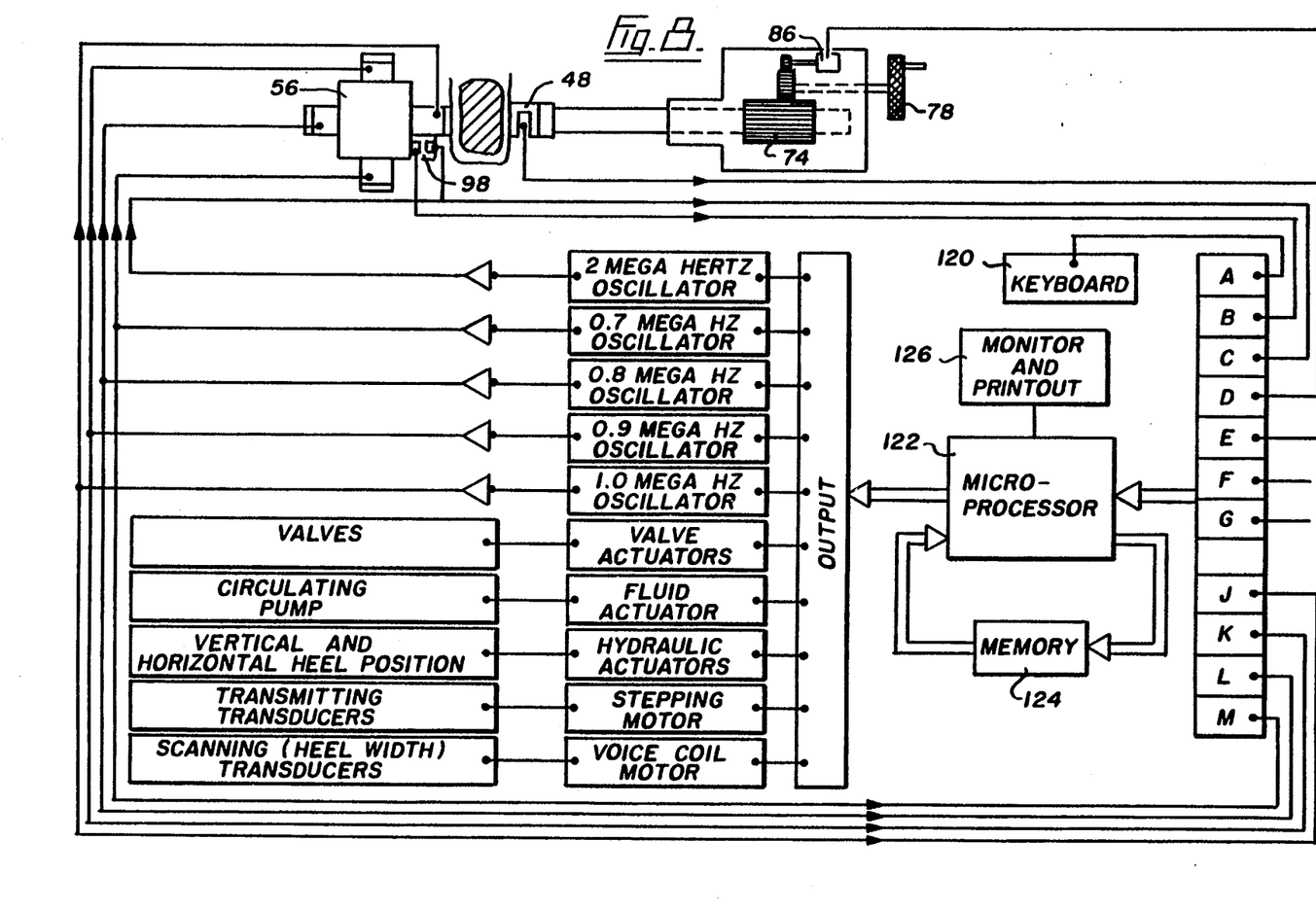
FIG. 8 shows schematically, the apparatus in association with the computer and control circuitry.

The control circuitry for the apparatus is shown in FIG. 8.

FIG. 8 shows a keyboard 120 to initiate the programme and insert the patient's name, age etc. There is a microprocessor 122. The microprocessor 122 is used to determine the center of the heel bone, compute the sound velocity by determining the time interval and distance, it adjusts the power output of all the transmitters 46, 50, 52, 54 to yield the same value of the receiver transducer output at zero distance by determining the pulse attitude and voltage. It compares the value with values received at the transmitter through the bone to determine attenuation at various frequencies. It relays instructions from a memory 124 to the operator through a monitor 126. It compares the pre-set temperatures with the actual bath and heat exchange temperatures. It controls all actuators with instructions from the keyboard or the programm's memory.

Memory 124 is used to store the data, the time of pulse release from the transmitter 46, the time the pulse is received at the receiver 48 and the revolutions of the counter 16 for the distance determination by the processor 122.

The information generated is input to the control circuitry as shown in FIG. 8. The input is as follows:

A. Allows inputting from the keyboard.

B. Receives the output from the scanning transducer 96.

C. Receives the information from the scanning transducer 96.

D. Receives the output from the receiving transducer.

E. Receives the output of the revolution counter 86.

F. Receives information concerning the bath temperature.

G. Receives information concerning the heat exchange temperature.

J. K. L. and M. respectively receive information from the 1 megahertz transmitter, 0.9 megahertz transmitter, 0.8 megahertz transmitter and 0.7 megahertz transmitter. This information is input to the microprocessor which generates an output signal and thus can send signals to the transmitters, valve actuators, fluid actuators to control the circulating pump, hydraulic actuators to operate the pump to control the bladders, the step motor that controls the transmitting transducers and the voice coil motor that controls the heel with the transducers.

To operate the illustrated apparatus, the apparatus is programmed to control automatically the temperature, to fill and empty the bath 12, to register time intervals and distances and to compute sound velocities and record patient names and similar data, all of which information is controlled as shown in FIG. 8. This apparatus that is illustrated schematically in FIG. 8, and the controlling software, is well known and is not described in detail here.

Liquid for the heat exchanger 44 and for the bath 12 are stored in the appropriate reservoirs 32 and 34 above the apparatus. The temperature in the bath 12 and the reservoir 34 is controlled at a temperature several degrees above heel temperature, the latter being 35° C. The heat exchanger 44 is kept at the same temperature as the liquid in the bath 12.

The hand wheel 78 is rotated to move the receiver 48 against the transmitter 46. On contact the reading is recorded as 0 distance. The appropriate signal is, of course, transmitted by the counter 86, through the line to the read-out 88. Any subsequent rotation of the wheel 78 in the opposite direction will be monitored by the revolution counter. The microprocessor shown in FIG. 8 converts the rotation to distance and displays this at the readout 88 in the body 10.

Zero distance is maintained and a pulse is transmitted by the transmitter 46. The time taken to reach the receiver 48 is recorded. This information is needed as the receiving transducer 48 is not at the zero position while the housing is. The time interval value is needed in computing the transit time across the bone alone.

While zero distance is maintained the step-motor 60 is programmed to rotate the housing 56 to each of its four positions. Each transducer 46, 50, 52 and 54 has its pulse rate raised and lowered by respective radio frequency amplifiers until a pre-determined but identical pulse amplitude is produced by the receiving transducer 48. This removes the error caused by a difference in efficiency of pulse conversion to voltage by the receiver at the varying frequencies. The instrument is now ready for use for the measurement of change in bone attenuation at these frequencies.

The patient's foot is cleaned, for example by a detergent, rinsed and thoroughly dried. A small quantity of wetting agent, for example a drop, is placed in the liquid in the bath. The foot is placed in the bath 12 and the strap 16 is fastened by virtue of buckle or hook and eye fastener, for example that available under the Trademark Velcro. In this position the heel abuts the transmitter 46. The wheel 78 is rotated to bring the receiver 48 housing against the heel on the opposite side. This distance is recorded by the revolution counter 86, which sends the appropriate signals to the microprocessor. This distance includes both the thickness of the skin and the bone and any underlying flesh. The motor 100 for the scanner 96 is operated, along with transducer 96. Its frequency is relatively high, about 2 megahertz, so that its energy is readily reflected by bone and only poorly by the soft tissue. The horizontal position of the heel bone is changed by the heel pad 22 by apparatus button 70 so that the pump fluid is pumped into and out of the pad 22. When the heel has been centred, the microprocessor records equal time intervals of reflection from the bone to the centre position of the scanning transducer. The result is displayed at readout 97.

Knob 28 is moved to pump fluid in or out of the sole pad 20. This raises or lowers the heel 10. When a minimum voltage is displayed on the monitor, maximum attenuation is obtained and this is the correct vertical position. This assures that the soft tissue below the heel bone is not part of the measurement.

The motor 100 is programmed to dwell on the central position of its scanning. The 2 megahertz scanning transducer 96 is automatically adjusted to produce the necessary amplitude of pulse. The time interval is recorded for a pulse to return by reflection from the bone surface, exactly double the time of one transit.

The lowest frequency transducer 46, at 0.7 megahertz, is used as higher frequencies are attenuated more in bone. The transducer 46 sends a burst of radio frequency energy and its time of travel to the receiving transducer 48 is recorded. The skin thickness transit time and the transit interval time zero distance are subtracted from this value to give the transit time through the heel bone alone. The corrected bone transit distance is divided by the correct transit time to yield a sound velocity in the human heel bone.

Thus the program may be summarized as follows:

1. Instrument calibration. Zero positions are determined and the step motor 60 is rotated to place the various transmitters 46, 50, 52, 54 in position and the response of the receiver 48 is compared to a pre-determined pulse level. The transmitters are adjusted by the microprocessor 122 until each transmitter produces the required value of the pulse at the receiver 48.

2. The hand wheel 78 is manually rotated to accommodate the heel.

3. Centering of the heel is carried out by activating the bladders 20 and 22. Scanning transducer 96 is used to verify that the correct position has been established.

4. A 1 megahertz pulse is sent from the transmitter 50. The time to the receiver 48 is recorded and velocity is thus calculated.

5. Attenuation is measured by measuring the pulse height at the receiver for each frequency, that is 0.7, 0.8, 0.9 and 1 megahertz.

6. The velocity is computed.

7. Attenuation at various frequencies is computed.

8. The composition percentage of normal, healthy young individuals and the percentage of the age group that is normal is compared.

With this information the diagnosis of osteoporosis may be made. The density and velocity of sound are high in a young, healthy adult. Accordingly values may be expressed as a percentage of the value of a group of young healthy adults. These values may be taken to be 100%. Values for healthy adults at various age levels may be determined and these values expressed as 100%. Values for patients can then be expressed as a percentage of a healthy young adult and a percentage of normal adults in their age groups. Thus true osteoporosis patients can be differentiated from normal osteoporosis which occurs as a result of aging.

The apparatus of the present invention prevents bubble formation within the bath 12 by maintaining the liquid in the bath at a temperature above the test object and above the temperature of the receiver 48 and transmitter 46. This is usually accomplished by heating the medium or, in the case of use in large bodies of water, for example under the sea, cooling of the components may take place. This is, for example, relevant in under water communications systems.

Bubble formation at an interface occurs when the liquid is at a lower temperature relative to the test object and the transmitter 46 and receiver 48. These bubbles result in unpredictable reflection scattering of sound energy.

The invention provides a more reliable and efficient ultrasound energy transference in the prior art. The invention thus has valuable applications in underwater communications, ultrasonic cleaning technology, shock wave lithotripping and areas where ever this energy is transferred using a liquid medium for coupling or transmitting the ultrasound.

Whereas previous methods utilize transducers, both for sending and receiving, these transducers were not only the same size but the area of receiving the sound energy was the entire face. The sensitivity of the transducer varies across the face. Thus a relatively high proportion of the received energy could arrive at an area of the transducer having a lower efficiency or sensitivity, resulting in inaccuracy. This is avoided by the concentration feature of the present invention.

The present invention also overcomes the problems of ultrasound energy transference by the prevention of bubble formation at the interface such as transducer to medium, medium to test object and medium to receiving transducer. This is achieved by raising the temperature of the liquid or coupling medium well above that of the transmitting transducer, the test object and the receiving transducer. Thus no gas release occurs at any of the interfaces and bubble formation is avoided. Extremely high attenuations are produced in water containing suspended gas bubbles. Viscous forces and heat conduction losses are associated with the compression and expansion of small gas bubbles and result in the loss of sound energy. Another effect of bubbles is a scattering of sound energy by absorption and re-radiation in all directions. The presence of gas bubbles changes the nature of the medium by altering its compressibility and so changes the velocity of sound through that medium. This also results in acoustic energy being reflected and refracted from the direction of the initial sound beam causing problems in all applications using a liquid medium for energy transfer. These problems are avoided in the present invention.

Although the invention describes particularly the use of the apparatus to diagnose osteoporosis, the apparatus and its principals are of value in underwater communications. In that environment the temperature of the transmitter and receiver are lowered by electronic cooling, as discussed above, or by circulating a cooling liquid within the main body. Therefore the sea will be at a higher temperature relative to the apparatus and bubble formation is prevented.

The invention also finds application in ultrasound cleaning technology. Again in the use of ultrasonic cleaning it is believed that there is a dissipation of sound energy by bubbles. However, the present invention, by heating the liquid in the cleaning tank, avoids bubble formation. Typically the method involves heating both the liquid externally. As bubbles are formed by heating they can be released. The liquid is then gravity drained and enters the tank from the bottom to prevent air from being trapped. Subsequently the liquid medium may have its temperature maintained at a lower temperature by coils within the tank. The objects to be cleaned should always be a lower temperature in the liquid medium to avoid bubble formation.

I claim:

1. Apparatus to measure the physical characteristics of a human foot, the apparatus comprising:
   a bath to receive the foot;
   a brace to receive the foot and to stabilize the position of the foot in the bath;
   a strap to hold the foot in the brace;
   means to pivotally mount the brace in the bath;
   a first bladder on the brace to contact the sole of the foot;
   a second bladder on the brace to contact the ankle of the foot;
   a fluid supply to said bladders;
   means to supply liquid to and from the bath;
   means to control temperature so that the liquid temperature is maintained above the temperature of the foot;
   ultrasonic transmitter means to send a signal through the foot;
   ultrasonic receiver means to receive the signal; and
   means to determine the velocity of the signal through the foot.

2. Apparatus as claimed in claim 1 in which the fluid supply is a liquid supply;
   a pump to pump the liquid to the bladders.

3. Apparatus as claimed in claim 1 including at least one reservoir to hold liquid for the bath;
   a pump to pump liquid between said at least one reservoir and the bath.

4. Apparatus as claimed in claim 3 including heating means in said at least one reservoir to control the temperature of the liquid.

5. Apparatus as claimed in claim 1 in which the ultrasonic transmitter means is a piezo-electric transmitter means.

6. Apparatus as claimed in claim 5 wherein said transmitter means comprises a plurality of transmitters mounted in a housing, each able to transmit a signal of different frequency.

7. Apparatus as claimed in claim 6 in which the housing is rotatable to use different transmitters.

8. Apparatus as claimed in claim 7 including a step motor to rotate said housing; and
   a transmission between said step motor and said housing.

9. Apparatus as claimed in claim 6 including means to input power to said housing.

10. Apparatus as claimed in claim 1 including means to reciprocate the receiver means to and from the transmitter means.

11. Apparatus as claimed in claim 10 in which the receiver means is mounted on a threaded shaft, received in a threaded housing;

a first gear wheel mounted on said threaded shaft;

a drive shaft able to be turned by hand;

a second gear wheel on said drive shaft to engage said first gear wheel whereby rotation of the drive shaft rotates the threaded shaft to reciprocate the shaft, and thus the receiver, relative to the housing.

12. Apparatus as claimed in claim 11 including means to record the distance moved by the receiver means.

13. Apparatus as claimed in claim 1 including means to focus the sound on to the receiver means that comprises a conical deflector upstream of the receiver means; and a parabolic reflector adjacent said conical deflector to direct the sound to the receiver means.

14. Apparatus as claimed in claim 1 including a transmitter/receiver unit able to transmit a signal towards the foot and receive the reflected signal, said signal being of such frequency that it can penetrate soft tissue but is reflected by bone.

15. Apparatus as claimed in claim 14 in which the transmitter means able to transmit a signal of about 2 megahertz.

16. Apparatus as claimed in claim 2 including a computer to control the apparatus.

* * * * *